United States Patent [19]

Ogawa

[11] Patent Number: 4,896,678
[45] Date of Patent: Jan. 30, 1990

[54] ENDOSCOPIC TREATING TOOL

[75] Inventor: Mototsugu Ogawa, Hachioji, Japan

[73] Assignee: Olympus Optical Co., Ltd., Tokyo, Japan

[21] Appl. No.: 130,490

[22] Filed: Dec. 9, 1987

[30] Foreign Application Priority Data

Dec. 12, 1986 [JP] Japan ................................ 61-296233

[51] Int. Cl.$^4$ .............................................. A61B 10/06
[52] U.S. Cl. ...................................... 128/751; 606/170
[58] Field of Search ............... 128/749, 751, 752, 753, 128/754, 755, 304–312, 348.1, 321; 604/273

[56] References Cited

U.S. PATENT DOCUMENTS

| | | | |
|---|---|---|---|
| 2,421,354 | 5/1947 | Reuter | 128/303 R |
| 2,437,014 | 3/1948 | Arnesen et al. | 128/303 R |
| 4,178,810 | 12/1979 | Takahashi | 128/751 |
| 4,467,802 | 8/1984 | Maslanka | 128/321 |
| 4,522,206 | 6/1985 | Whipple et al. | 128/305 |
| 4,586,496 | 5/1986 | Keller | 128/305 |
| 4,674,501 | 6/1987 | Greenberg | 128/305 |
| 4,712,547 | 12/1987 | Bonnet | 128/305 |
| 4,763,668 | 8/1988 | Macek et al. | 128/751 |
| 4,785,825 | 11/1988 | Romaniuk | 128/751 |

FOREIGN PATENT DOCUMENTS

| | | | |
|---|---|---|---|
| 2126705 | 12/1971 | Fed. Rep. of Germany ... | 128/305 R |
| 2558570 | 7/1976 | Fed. Rep. of Germany ...... | 128/321 |
| 2735706 | 10/1979 | Fed. Rep. of Germany . | |
| 3343867 | 6/1985 | Fed. Rep. of Germany ...... | 128/305 |
| 233302 | 2/1986 | German Democratic Rep. ..................... | 128/751 |
| 57-193811 | 9/1982 | Japan . | |
| 57-40964 | 12/1982 | Japan . | |
| 618108 | 8/1978 | U.S.S.R. .............. | 128/751 |

Primary Examiner—Max Hindenburg
Assistant Examiner—K. M. Reichle
Attorney, Agent, or Firm—Armstrong, Nikaido, Marmelstein, Kubovcik & Murray

[57] ABSTRACT

Endoscopic treating tool in which structure is provided for completely releasing the transmission of force to a treatment part of the tool adjacent a tip end of an insertable part of the tool from the operating member provided at a base side of the insertable part when the operating force for the operating member becomes larger than a predetermined amount.

16 Claims, 6 Drawing Sheets

FIG. 5
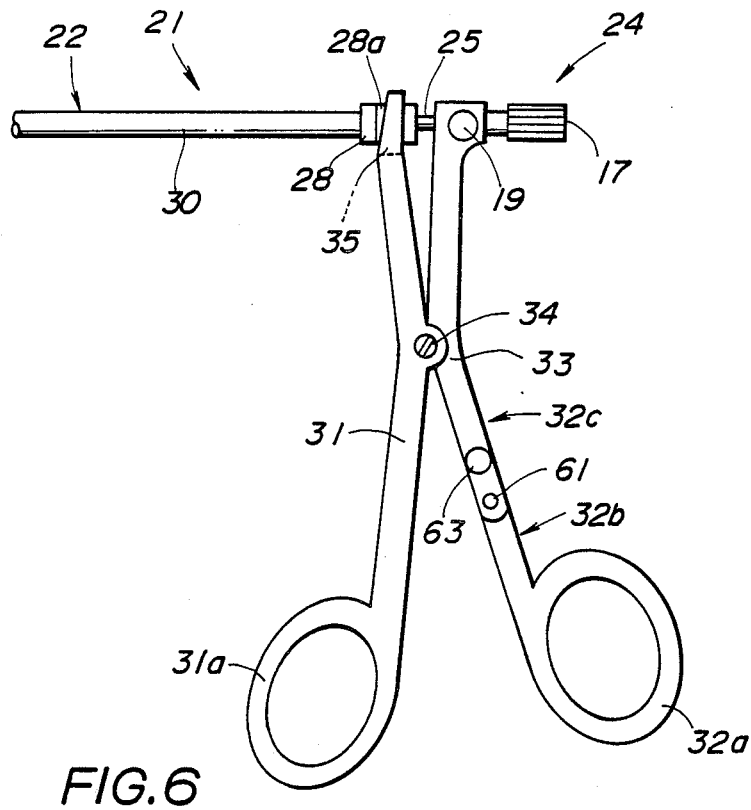
FIG. 6
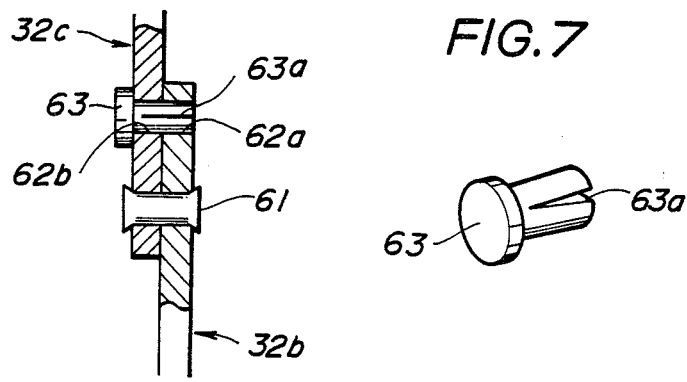
FIG. 7

4,896,678

ENDOSCOPIC TREATING TOOL

BACKGROUND OF THE INVENTION

1. Field of the Invention

This invention relates to a treating tool useable with an endoscope which is not damaged or broken in case an excess operating force is applied.

2. Related Art Statement

Recently, medical endoscopes have become widely used whereby an organ or the like within a body cavity of a patient can be observed by inserting the endoscope into the body cavity. A treatment can be made using a treating tool by inserting an elongated insertable part of the tool through a treating tool channel of the endoscope as required. Also, in the industrial field, industrial endoscopes are being widely used whereby the interior of a boiler, turbine, engine or chemical plant can be observed.

Various different treating tools can be used as accessories together with or independently of the above mentioned endoscope such as a biopsic forceps or a holding forceps. A biopsic forceps is shown, for example, in the gazette of Japanese utility model application laid open No. 193811/1982. FIG. 11 is an elevation showing this biopsic forceps. A biopsic forceps 1 is formed of a sheath 2, a treating part 3 provided adjacent the tip part of this sheath and an operating part 4 provided in the base end part of the sheath 2. The sheath 2 consists of a pipe 10 through which an operating shaft 5 as shown in FIG. 12 is inserted. A pair of biopsic cups 6 and 7 are fitted by brazing or the like to the tip part of this operating shaft 5. These biopsic cups 6 and 7 are formed of a pair of holding pieces 6a and 7a which are resilient tending to separate and open them to be in the form of V. Cup-like cutting blades 6b and 7b are formed at the open ends of these holding pieces 6a and 7a. A male screw part 5a is formed in the rear end part of the operating shaft 5.

A base member 8 having an engaging part 8a on the sides is fixed to the rear end part of the sheath 2. A pair of handles 11 and 12 having finger loops 11a and 12a and being pivoted at their center portions 13 with a pivoting pin 14 without intersecting with each other are provided as the operating part 4. A U-like groove 15 is formed in the tip part of the front side handle 11 and is engaged with the engaging part 8a of the base member 8. An inserting hole through which the operation shaft 5 is inserted in the rear end part is formed in the tip part of the rear side handle 12. The operating shaft 5 is inserted in the rear end part through this inserting hole and projects on the rear side of the handle 12. A stopper screw 17 for stopping the escape of this operating shaft 5 is screwed to a male screw part 5a of the operating shaft 5.

Further, a screw hole intersecting at right angles with the inserting hole is provided in the tip part of the handle 12. A fixing screw 19 fixing the operating shaft 5 is screwed in this screw hole so that the forward and rearward position of the operating shaft 5 may be adjustable.

In such formation, when the finger loops 11a and 12a of the handles 11 and 12 are operated in the opening direction (that is, apart from each other), the tip parts of the handles 11 and 12 will move in the closing direction (that is, towards each other) and the pipe 10 will move rearward with respect to the operating shaft 5. Then, the holding pieces 6a and 7a will project out of the pipe 10 and will open in the form of V. When the finger loops 11a and 12a of the handles 11 and 12 are operated in the closing direction, the holding pieces 6a and 7a will be retracted into pipe 10 and the cutting blades 6b and 7b will come together so that a sample of living body tissue may be collected.

Now, in using the above described biopsic forceps 1, in such case that the tissue to be collected is hard, if an excess force is applied to the handles 11 and 12, the biopsic cups 6 and 7 of the treating part 3 are likely to be broken.

A technique wherein an operating mechanism is provided with a flexible coil so that an excess force applied to the operating part may be absorbed by the flexible coil is disclosed, for example, in the gazette of Japanese utility model laid open No. 40964/1982 or in the West German patent application No. 2735706.

However, in the above mentioned related technique, all of the excess force will not be absorbed by the flexible coil and a part of the excess force will be applied to the operating wire and biopsic cups and therefore the biopsic cups and others will not be able to be perfectly prevented from being broken.

OBJECT AND SUMMARY OF THE INVENTION

An object of the present invention is to provide an endoscopic treating tool having structure which can prevent the treating part from being damaged or broken by an excess operating force when applied.

The endoscopic treating tool of the present invention comprises an elongated insertable part insertable through a treating tool channel or the like in an endoscope, a treating means provided adjacent the tip part of the insertable part, an operating means provided on the base side of the insertable part for operating the treating means and a force transmitting means connecting the operating means and treating means with each other and making the treating means operatable by the operation of the operating means and is provided with an operation releasing means for completely releasing the transmission of the force from the operating means to the treating means when the operating force for the operating means becomes larger than is predetermined. In case an excess force is applied to the operating means, the transmission of the operating force to the treating means will be released by the operation releasing means.

The other features and advantages of the present invention will become apparent enough with the following description.

BRIEF DESCRIPTION OF THE DRAWINGS

FIG. 1 is a sectioned view of an essential part of a biopsic forceps.

FIG. 2 is a side view of the biopsic forceps with biopsic cups opened.

FIG. 3 is a side view of the biopsic forceps with the forceps cups closed.

FIGS. 5 to 7 relate to the third embodiment of the present invention.

FIG. 5 is a side view showing an operating part of a biopsic forceps.

FIG. 6 is a partly sectioned view showing a part of a handle.

FIG. 7 is a perspective view showing an adjusting pin.

FIG. 11 is a side view of a biopsic forceps.

FIG. 12 is a side view showing an operating shaft and biopsic cups.

DETAILED DESCRIPTION OF THE PREFERRED EMBODIMENTS

Figure 1:
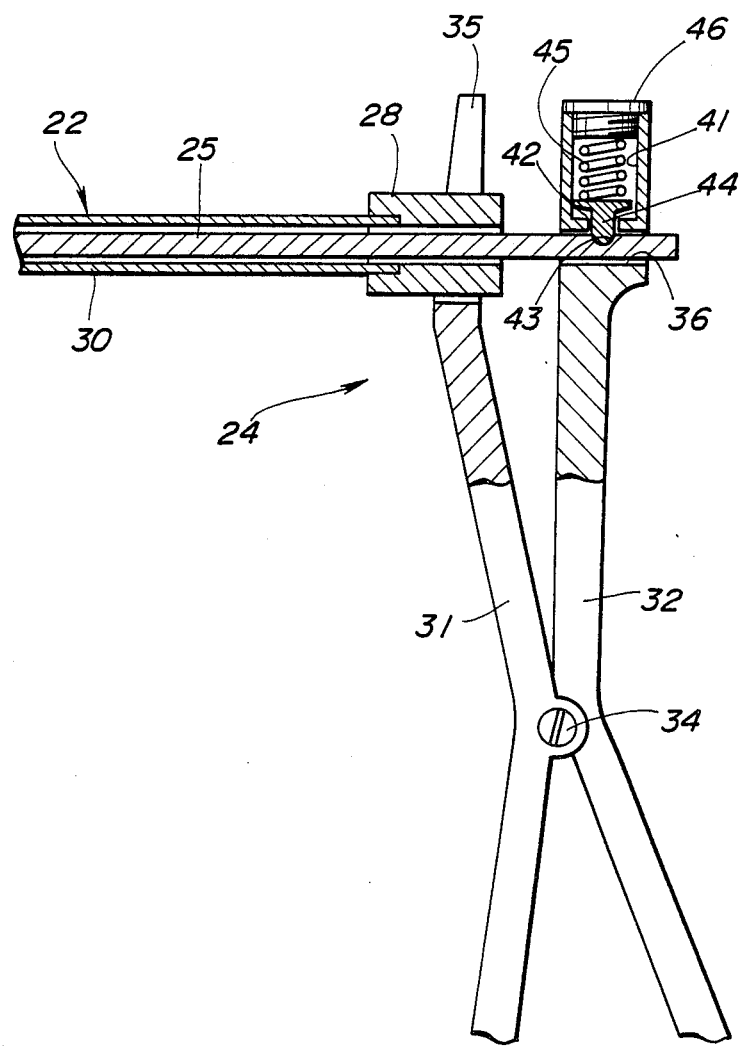
FIGS. 1 to 3 relate to the first embodiment of the present invention.
Figure 2:
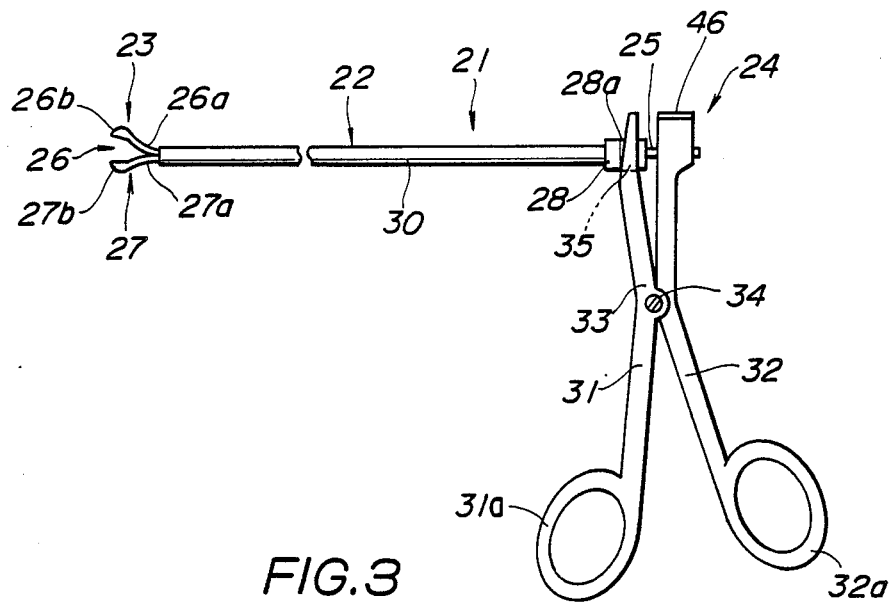
Figure 3:
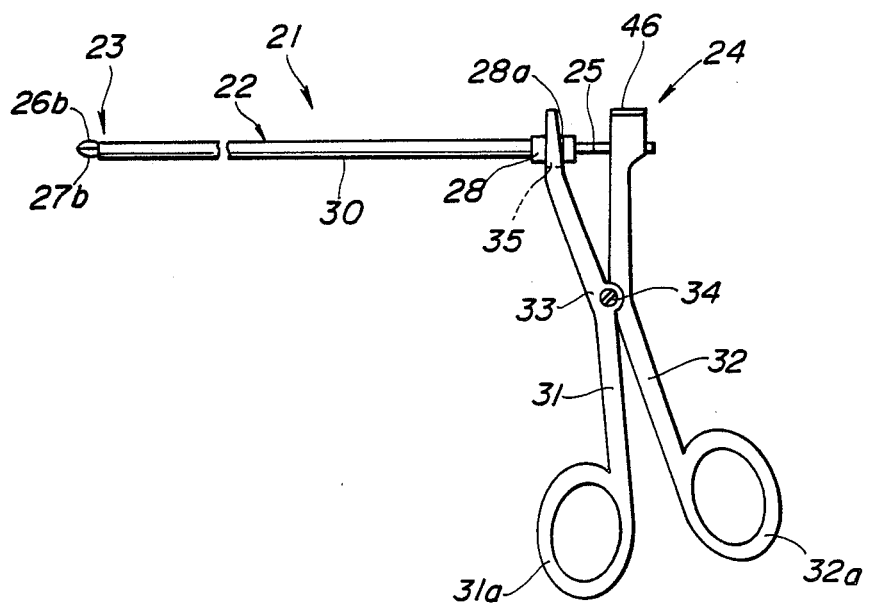

The First embodiment of the present invention is shown in FIGS. 1 to 3.

As shown in FIGS. 2 and 3, a biopsic forceps 21 is formed of a sheath 22, a treating part 23 provided adjacent the tip part of this sheath 22 and operating part 24 provided in the base end part of the sheath 22. The sheath 22 consists of a pipe 30 through which an operation shaft 25 as a force transmitting member is inserted. This operating shaft is made, for example, of a metal bar and is fitted in the tip part with a pair of biopsic cups 26 and 27 forming a treating part 23 by brazing or the like. These biopsic cups 26 and 27 are formed of holding pieces 26a and 27a having such resiliency as to separate and open them to be in the form of V and cup-like cutting blades 26b and 27b formed at the open ends of these holding pieces 26a and 27a. The biopsic cups 26 and 27 may be separate from the operating shaft 25 or may be formed of a metal or the like to be integral with the operating shaft 25.

A base member 28 having an engaging part 28a on the sides is fixed to the rear end part of the sheath 22. The operating part 24 has finger loops 31a and 32a and is provided with a pair of handles 31 and 32 as operating members pivoted with a pivoting pin 34 at their center portions 33 without intersecting with each other. A u-like groove 35 is formed in the tip part of the front side handle 31 and is engaged with the engaging part 28a of the base member 28. As shown in FIG. 1, an inserting hole 36 through which the operating shaft 25 is to be inserted in the rear end part is formed in the tip part of the rear side handle 32. The operating shaft 25 is inserted in the rear end part through this inserting hole 36 and projects on the rear side of the handle 32.

In this embodiment, as shown in FIG. 1, a recess 41 opening on the tip side is provided in the tip part of the handle 32. A communicating hole 42 communicating with the inserting hole 36 is formed in the bottom of this recess 41. An engaging groove 43 is formed in the position corresponding to the communicating hole 41 in the side part on the rear end side of the operating shaft 25. An engaging pin 44 is contained in the recess 41 and is inserted on the tip side through the communicating hole 42. The engaging pin 44 projects on the inserting hole 36 side and is engaged with the engaging groove 43 of the operating shaft 25. The operating shaft 25 and handle 32 are connected with each other by the engagement of this engaging pin 44 with the engaging groove 4. A spring 45 biasing the engaging pin 44 to the above mentioned inserting hole 36 side is contained in the recess 41. A lid 46 is screwed to the opening part of the recess 41. The spring 45 is held with the recess 41 by this lid 46. The biasing force of the spring 45 is of such size that, when a force larger than is predetermined is applied in the axial direction of the operating shaft 25 to the engaging part of the engaging groove 43 and engaging pin 44, the engaging groove 43 and engaging pin 44 will be disengaged from each other. The biasing force of the spring 45 can be adjusted by the lid 46. The predetermined force is a force smaller than the force applied when the biopsic cups 26 and 27 of the treatment part 23 are damaged or broken.

In this embodiment formed as in the above, as shown in FIG. 2, when the finger loops 31a and 32a of the handles 31 and 32 are operated in the opening direction, the tip parts of the handles 31 and 32 will move in the closing direction and the pipe 30 will more rearward with respect to the operating shaft 25. Then, the holding pieces 26a and 27a of the biopsic cups 26 and 27 will project out of the pipe 30 to separate and open in the form of V. As shown in FIG. 3, when the finger loops 31a and 32a of the handles 31 and 32 are operated in the closing direction, the holding pieces 26a and 27a will be contained within the pipe 30 and the cutting blades 26b and 27b come together so that the sample of living body tissue may be collected.

In this embodiment, in such case that the tissue to be collected is hard, when an excess force is applied and the operating force for the handles 31 and 32 becomes larger than is predetermined, the engaging groove 43 of the operating shaft 25 and the engaging pin 44 will disengaged from each other. That is to say, the handle 32 and operating shaft 25 will be disconnected from each other and the operating force for the handles 31 and 32 will be no longer transmitted to the treating part 23. Therefore, the biopsic cups 26 and 27 of this treating part 23 can not be pulled with a force larger than is predetermined and will be prevented from being damaged or broken.

Also, in this embodiment, when the operating force for the handles 31 and 32 becomes larger than is predetermined and the engaging groove 43 of the operating shaft 25 and the engaging pin 44 are disengaged from each other, when the engaging groove 43 of the operating shaft 25 and the engaging pin 44 are again engaged with each other, the forceps will be able to be simply re-used.

Figure 4:
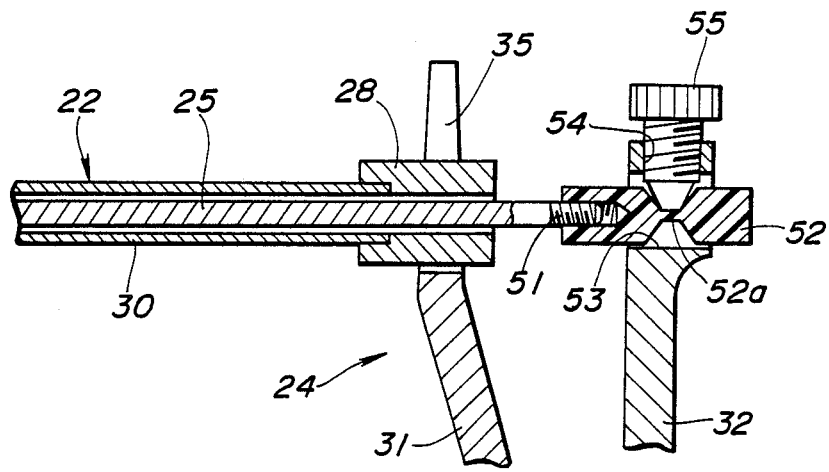
FIG. 4 is a sectioned view of an essential part of a biopsic forceps of the second embodiment of the present invention.

The second embodiment of the present invention is shown in FIG. 4.

In this embodiment, a male screw part 51 is formed in the rear end part of the operating shaft 25 and a connector 52 is screwed to this male screw part 51. This connector 52 is made of plastics or metal, is formed to be substantially columnar on the whole and has a thin diameter part 52a formed in a substantially middle part in the axial direction. An inserting hole 53 through which the connector 52 is inserted is formed in the tip part of the rear side handle 32. The connector 52 is inserted through this inserting hole 52 and is projected on the rear side of the handle 32. A female screw part 54 communicating with the inserting hole 53 from the tip side is provided in the tip part of the handle 32. A fixing screw 55 is screwed into this female screw part 54 and is engaged in the tip part with the thin diameter part 52a of the connector 52 so that the operating shaft 25 and handle 32 may be connected with each other through the connector 52. The thin diameter part 52a is so made as to break when the axial pulling force becomes larger than a predetermined force. The predetermined force is a force smaller than the force applied when the biopsic cups 26 and 27 of the treating part 23 are damaged or broken.

In this embodiment, when the operating force for the handles 31 and 32 becomes larger than the predetermined force, the thin diameter part 52 of the connector 52 will break, the handle 32 and operating shaft 25 will be thereby disconnected from each other and the operating force for the handles 31 and 32 will be no longer transmitted to the treating part.

In this embodiment, when the operating force for the handles 31 and 32 becomes larger than is predetermined and the thin diameter part 52a of the connector 52 is broken, the connector 52 can be replaced to enable simple re-use of the tool.

The other formations, operations and effects are the same as in the first embodiment.

The third embodiment of the present invention is shown in FIGS. 5 to 7.

In this embodiment, a male screw part is formed in the rear end part of the operating shaft 25. An inserting hole through which the operating shaft 25 is inserted in the rear end part is formed through the tip part of the rear side handle 32. The operating shaft 25 is inserted in the rear end part through this inserting hole and is projected on the rear side of the handle 32. A stopper screw 17 for stopping the escape of this operating shaft 25 is screwed to the male screw part of the operating shaft 25.

Further, a screw hole intersecting at right angles with the inserting hole is provided in the tip part of the handle 32 and a fixing screw 19 fixing the operating shaft 25 is screwed in this screw hole so that the forward and rearward position of the operating shaft 5 may be adjustable.

Further, as shown in FIG. 6, in this embodiment, the rear side handle 32 is divided into a base part 32b and an opposite base part 32c between the middle part 33 and finger loop 32a. The base part 32b and opposite base part 32c are rotatably connected with each other through a fixing pin 61. Communicating pin holes 62a and 62b are formed respectively in the tip part of the base part 32b and in the opposite base part 32c. An adjusting pin 63 is inserted in these pin holes 62a and 62b so as to regulate the rotation of the base part 32b and opposite base part 32c. the adjusting pin 63 is made of plastics or the like, has a slit part 63a formed in the axial direction and is so made as to be broken or to escape out of the pin holes 62a and 62b when the force in the rotating direction with the fixing pin 61 as a center becomes larger than a predetermined force. The predetermined force is a force smaller than the force applied when the biopsic cups 26 and 27 of the treating part 23 are damaged or broken.

In this embodiment, when the operating force for the handles 31 and 32 becomes larger than the predetermined force, the adjusting pin 63 will be broken or will escape out of the pin holes 62a and 62b, the base part 32b and opposite base part 32c of the handle 32 will become rotatable and the operating force for the handles 31 and 32 will be no longer transmitted to the treating part 23.

Also, in this embodiment, when the operating force for the handles 31 and 32 become larger than is predetermined and the adjusting pin 63 is broken in the thin diameter part 63a or escapes out of the pin holes 62a and 62b, the above mentioned adjusting pin 63 can be replaced to enable simple re-use of the tool.

The other formations, operations and effects are the sample as in the first embodiment.

Figure 8:
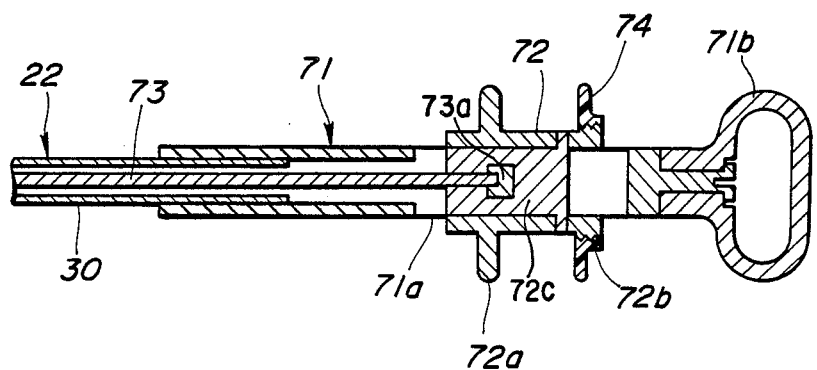
FIG. 8 is a sectioned view showing an operating part of a biopsic forceps of the fourth embodiment of the present invention.

The fourth embodiment of the present invention is shown in FIG. 8.

In this embodiment, an operating part body 71 is connected to the rear end part of the sheath 22 and is formed of a slotted sheath part 71a and a finger ring 71b formed on the rear end of this shaft part 71a. A slider 72 is slidably externally fitted on the operating part body 71 and includes a slider member 72c extending through the slotted shaft part 71a. An operating wire 73 as a force transmitting member is connected at the rear end to this slider member 72c by a lug 73a anchored therein. On the outer peripheral part of the slider 72, a thick finger engaging part 72a is formed on the front end side and a male screw part 72b is formed on the rear end side. A thin finger engaging member 74 is screwed to this male screw part 72b. This finger engaging member 74 is made of plastics or the like and is so made as to buckle when the force in the axial direction becomes larger than a predetermined force. The predetermined force is a force smaller than the force applied when the biopsic cups 26 and 27 of the treating part 23 are damaged or broken.

In this embodiment, when a thumb is hung on the finger ring 71b of the operating part body 71, a pointing finger and middle finger of the same hand are hung on the slider 72 and this slider 72 is slide forward and rearward along the shaft part 71a of the operating part body 71, the operating wire 73 will move in the axial direction and the biopsic cups 26 and 27 of the treating part 23 will be operated to open and close.

In this embodiment, when the slider 72 is pulled too strongly and this operating force becomes larger than is predetermined, the thin finger engaging member 74 will buckle and the operation will become impossible.

Also, in this embodiment, when the finger engaging member 74 has buckled, this finger engaging member 74 can be replaced to enable simple re-use of tool.

The other formations, operations and effects are the same as in the first embodiment.

Figure 9:
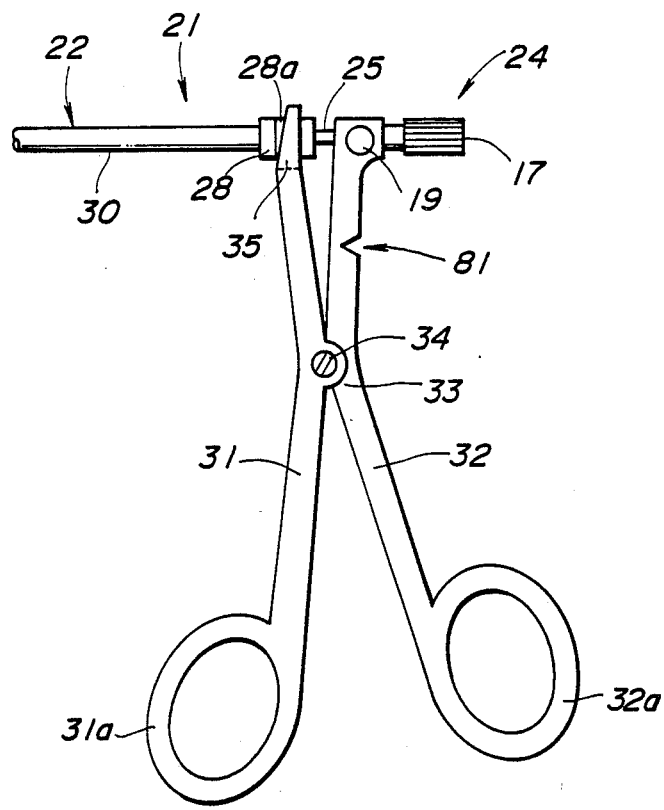
FIG. 9 is a side view showing an operating part of a biopsic forceps of the fifth embodiment of the present invention.

The fifth embodiment of the present invention is shown in FIG. 9.

In this embodiment, a notch 81 is formed between the center portion 33 and tip part of the rear side handle 32. When the operating force for the handles 31 and 32 becomes larger than is predetermined, the handle 32 will buckle at the notch 81.

The other formations, operations and effects are the same as in the first embodiment.

Figure 10:
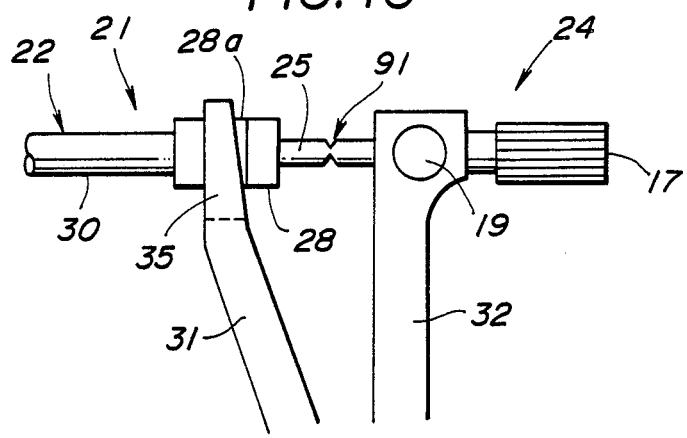
FIG. 10 is a side view showing an essential part of a biopsic forceps of the sixth embodiment of the present invention.
Figure 11:
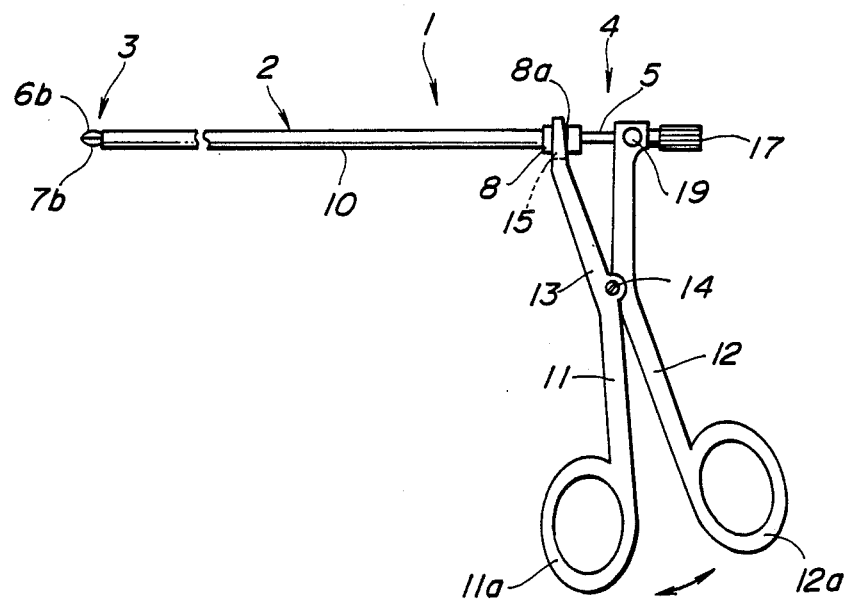
FIGS. 11 and 12 relate to a related art example.
Figure 12:
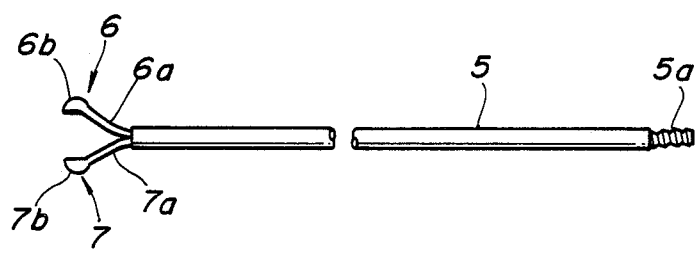

The sixth embodiment of the present invention is shown in FIG. 10.

In this embodiment, a peripheral notch 91 is formed on the rear end side of the operating shaft 25. When the operating force for the handles 31 and 32 becomes larger than is predetermined, the operating shaft 25 will break at the notch 91.

The other formations, operations and effects are the same as in the first embodiment.

The present invention is not limited to the above mentioned embodiments. For example, in FIG. 1, when the operating force for the handles 31 and 32 becomes larger than is predetermined, the connection between the pipe 30 forming the sheath 22 and the front side handle 31 may be released.

The present invention can be applied not only to a biopsic forceps but also to various treating tools such as a holding forceps having holding cups or holding pawls at the tip, a busket-type holding forceps and a high frequency electric knife having a wire loop for incision and operating this wire loop to open and close.

As explained above, according to the present invention, as there is provided an operation releasing means whereby, when the operating force for the operating member becomes larger than is predetermined, the transmission of the force from the above mentioned operating member to the treating part will be released, there is an effect that the treating part can be positively prevented from being damaged or broken in case an excess operating force is applied.

In this invention, it is apparent that working modes different in a wide range can be formed on the basis of this invention without deviating from the spirit and scope of the invention. This invention is not restricted by its specific working mode except being limited by the appended claims.

What is claimed is:

1. An endoscopic treating tool for use with an endoscope comprising:
   an elongated insertable part having a distal part insertable through the endoscope, and an opposite proximal part remaining outside the endoscope;
   a treating means requiring an operation force to be applied thereto for treating a patient, provided adjacent the distal part of said insertable part;
   an operating means provided on the proximal part of said insertable part to which force is applied for operating the treating means;
   a force transmitting means connecting said operating means and said treating means with each other so as to make said treating means operable by operation of said operating means; and
   an operation force releasing means for completely releasing the transmission of force to said treating means from said operating means when the operating force for said operating means becomes larger than a predetermined force.

2. An endoscopic treating tool according to claim 1 wherein said operation force releasing means includes connecting means for connecting said operating means and said force transmitting means directly with each other so that said operating means and said force transmitting means are disconnected from each other in case a force larger than said predetermined force is applied.

3. An endoscopic treating tool according to claim 2 wherein said insertable part comprises a pipe; said force transmitting means comprises a shaft slideably and coaxially mounted in said pipe having a distal end and a proximal end slideably extending out of said pipe; said treating means includes a pair of holding pieces having free ends provided at said distal end of said shaft, extendible out of the distal part of said insertable part and having such resiliency as to separate and open said holding pieces to be in the form of a V with each other when extended out of said insertable part and cutting blades provided at the free ends of said holding pieces; and said operating means comprises a pair of handles, each having a tip part at one end, a center portion, and a finger loop at the other end, said handles being non-crossingly pivoted together at their center portions, the tip part of one handle being connected to said proximal end of said shaft through said connecting means and the tip part of the other handle being connected to said proximal part of said insertable part.

4. An endoscopic treating tool according to claim 3 wherein said connecting means includes a recess provided on said proximal end of said shaft, pin means provided in said tip part of said one handle, at a position corresponding to the position of said recess, for engaging with and disengaging from said recess, and means for biasing said pin means to engage said recess so that, when said pin means is engaged with said recess said one handle and said shaft will be connected with each other and, when a force larger than said predetermined force is applied, said pin means will disengage from said recess.

5. An endoscopic treating tool according to claim 3 wherein said connecting means comprises a connector replaceably connected to the proximal end of said shaft, thin diameter means being formed on said connector for breaking when a pulling force larger than said predetermined force is applied, and fixing means provided on said one handle, for engaging with said thin diameter means and connecting said one handle and said shaft with each other when engaged with said thin diameter means.

6. An endoscopic treating tool according to claim 1 wherein said operation force releasing means comprises bucklable means provided on said operating means for buckling when a force larger than said predetermined force is applied to said operating means.

7. An endoscopic treating tool according to claim 6 wherein said insertable part comprises a pipe; said force transmitting means comprises a shaft slideably and coaxially mounted in said pipe having a distal end and a proximal end slideably extending out of said pipe; said treating means includes a pair of holding pieces having free ends provided at said distal end of said shaft, extendible out of the distal part of said insertable part and having such resiliency as to separate and open said holding pieces to be in the form of a V with each other when extended out of said insertable part and cutting blades provided at the free ends of said holding pieces; and said operating means comprises a pair of handles, each having a tip part at one end, a center portion, and a finger loop at the other end, said handles being non-crossingly pivoted together at their center portions, the tip part of one handle being connected to said proximal end of said shaft through said connecting means and the tip part of the other handle being connected to a said proximal part of said insertable part.

8. An endoscopic treating tool according to claim 7 wherein said bucklable means is provided on said one handle, and said one handle further comprises two portions which overlap each other and are pivotably connected thereat, a communicating hole being provided through the overlapping portions of said two members, and said bucklable means includes pin means inserted in said hole or breaking or escaping out of said hole when a force larger than said predetermined force is applied to said one handle.

9. An endoscopic treating tool according to claim 6 wherein said insertable part comprises a sheath; said force transmitting means comprises a wire slideably and coaxially mounted in said sheath having a distal end and a proximal end slideably extending out of said sheath; said treating means comprises a pair of holding pieces having free ends provided at said distal end of said wire, extendable out of the distal part of the insertable part and having such resiliency as to separate and open said holding pieces to be in the form of a V with each other when extended out of said insertable part and cutting blades provided at the free ends of said holding pieces; and said operating means includes operating body means connected to said proximal part of said insertable part, slider means provided slidably on said operating body means and connected to said proximal end of said wire and finger engaging part means provided on the slider means for sliding said slider means.

10. An endoscopic treating tool according to claim 9 wherein said bucklable means comprises said finger engaging means which is formed to be thin so as to be bucklable and which is replaceably fitted to said slider means.

11. An endoscopic treating tool according to claim 1 wherein said operation force releasing means comprises breakable means provided on said operating means for breaking when a force larger than said predetermined force is applied.

12. An endoscopic treating tool according to claim 11 wherein said insertable part comprises a pipe; said force transmitting means comprises a shaft slideably coaxially mounted in said pipe having a distal end and a proximal end slideably extending out of said pipe; said treating means includes a pair of holding pieces having free ends provided at said distal end of said shaft, extendible out of the distal part of said insertable part and having such resiliency as to separate and open said holding pieces to be in the form of a V with each other when extended out of said insertable part and cutting blades provided at the free ends of said holding pieces; and said operating means comprises a pair of handles, each having a tip part at one end, a center portion, and a finger loop at the other end, said handles being non-crossingly pivoted together at their center portions, the tip part of one handle being connected to said proximal end of said shaft through said connecting means and the tip part of the other handle being connected to said proximal part of said insertable part.

13. An endoscopic treating tool according to claim 12 wherein said breakable means in the form of a notch provided on said one handle.

14. An endoscopic treating tool according to claim 1 wherein said operation force releasing means comprises breakable means provided on said force transmitting means for breaking when a force larger than said predetermined force is applied.

15. An endoscopic treating tool according to claim 14 wherein said insertable part comprises a pipe; said force transmitting means comprises a shaft slideably and co-axially mounted in said pipe having a distal end and a proximal end slideably extending out of said pipe; said treating means includes a pair of holding pieces having free ends provided at said distal end of said shaft, extendible out of the distal part of said insertable part and having such resiliency as to separate and open said holding pieces to be in the form of a V with each other when extended out of said insertable part and cutting blades provided at the free ends of said holding pieces; and said operating means comprises a pair of handles, each having a tip part at one end, a center portion, and a finger loop at the other end, said handles being non-crossingly pivoted together at their center portions, the tip part of one handle being connected to said proximal end of said shaft through said connecting means and the tip part of the other handle being connected to said proximal part of said insertable part.

16. An endoscopic treating tool according to claim 15 wherein said breakable means in the form of a notch provided on said shaft.

* * * * *